United States Patent [19]
Barbacid et al.

[11] Patent Number: 5,919,650
[45] Date of Patent: Jul. 6, 1999

[54] METHOD FOR INACTIVATION OF PROTEIN FUNCTION

[75] Inventors: Mariano Barbacid, Lawrenceville; Ximena Montano, Cranbury, both of N.J.

[73] Assignee: Bristol-Myers Squibb Co., New York, N.Y.

[21] Appl. No.: 07/690,192

[22] Filed: Apr. 22, 1990

[51] Int. Cl.⁶ .............................. C12P 21/06; C12N 15/13
[52] U.S. Cl. ........................ 435/69.1; 435/330; 435/320.1
[58] Field of Search ................................. 435/6; 436/508, 436/804; 424/3

[56] References Cited

PUBLICATIONS

Biocca et al. 1990. Expression and targeting of intracellular ab in mammalian cells EMBO Journal 9:101–108.
Carlson, J.R. 1988. A New Means of Inducibly Inactivating a Cellular Protein, Mol. Cell. Biol. 8:2638–2646.
Emorine and Max 1983 Structural Analysis of a rabbit immunoglobulin κ2 J–C. locus reveals multiple deletions Nuc. Acids Res. 11:8877.
Sheppard & Gutman 1981. Allelic forms of rat κ chain genes: Evid. for strong sel. at level of nucleo. seq. PNAS. 78: 7064–7068.
Pulciani et al. ras Gene Amplification and Malignant Transformation, Mol. Cell. Biol. 5: 2836.
Altenburger et al. Functional & Nonfunctional joining in immunogl. light chain genes of a mouse myeloma, Nature 287:603.
Brüggemann M. 1988. Evolution of the rat immunogl. gamma heavychain gene family Gene 74:473–482.

*Primary Examiner*—Karen Cochrane Carlson
*Attorney, Agent, or Firm*—James M. Bogden; Timothy J. Gaul; Audrey F. Sher

[57] ABSTRACT

Method for inactivating the function produced by a protein using an intracellularly expressed antibody or fragment thereof.

12 Claims, 12 Drawing Sheets

METHOD FOR INACTIVATION OF PROTEIN FUNCTION

BACKGROUND OF THE INVENTION

It is presently known that many human diseases are caused at least in part by proteins present in the cells of the afflicted individual. For example, certain proteins encoded by oncogenes are known to be responsible for the production of cancer in humans.

Neoplasia is a process by which the normal controlling mechanisms that regulate cell growth and differentiation are impaired resulting in progressive growth. During neoplasia, there is a characteristic failure to control cell turnover and growth. This lack of control causes a tumor to grow progressively, enlarging and occupying space in vital areas of the body. If the tumor invades surrounding tissue and is transported to distant sites, death of the individual often results.

The preferential killing of cancer cells without deleterious effect on normal cells is the desired goal in cancer therapy. In the past this has been accomplished using a variety of procedures. These procedures include the administration of chemicals, chemotherapy, radiation, radiotherapy, and surgery.

Recently there has been a rapid expansion of cancer treatments. Even though new treatments are being developed, the need still exists for improved methods for the treatment of most types of cancers.

SUMMARY OF THE INVENTION

The present invention concerns a method for inactivating the function of a protein by introducing one or more recombinant DNA molecules encoding an antibody or fragment thereof which specifically binds the protein into a cell (e.g., a mammalian cell) which expresses the protein, expressing the recombinant DNA molecules encoding the antibody or fragment thereof intracelluarly and allowing the antibody or fragment thereof to specifically bind the protein so that the function of the protein is inactivated.

The method of the present invention is useful for eliminating an undesirable biological response (e.g., cancer) produced by the protein, and is particularly applicable to the treatment of neoplastic cells, such as cancer cells.

DETAILED DESCRIPTION OF THE INVENTION

Figure 1:
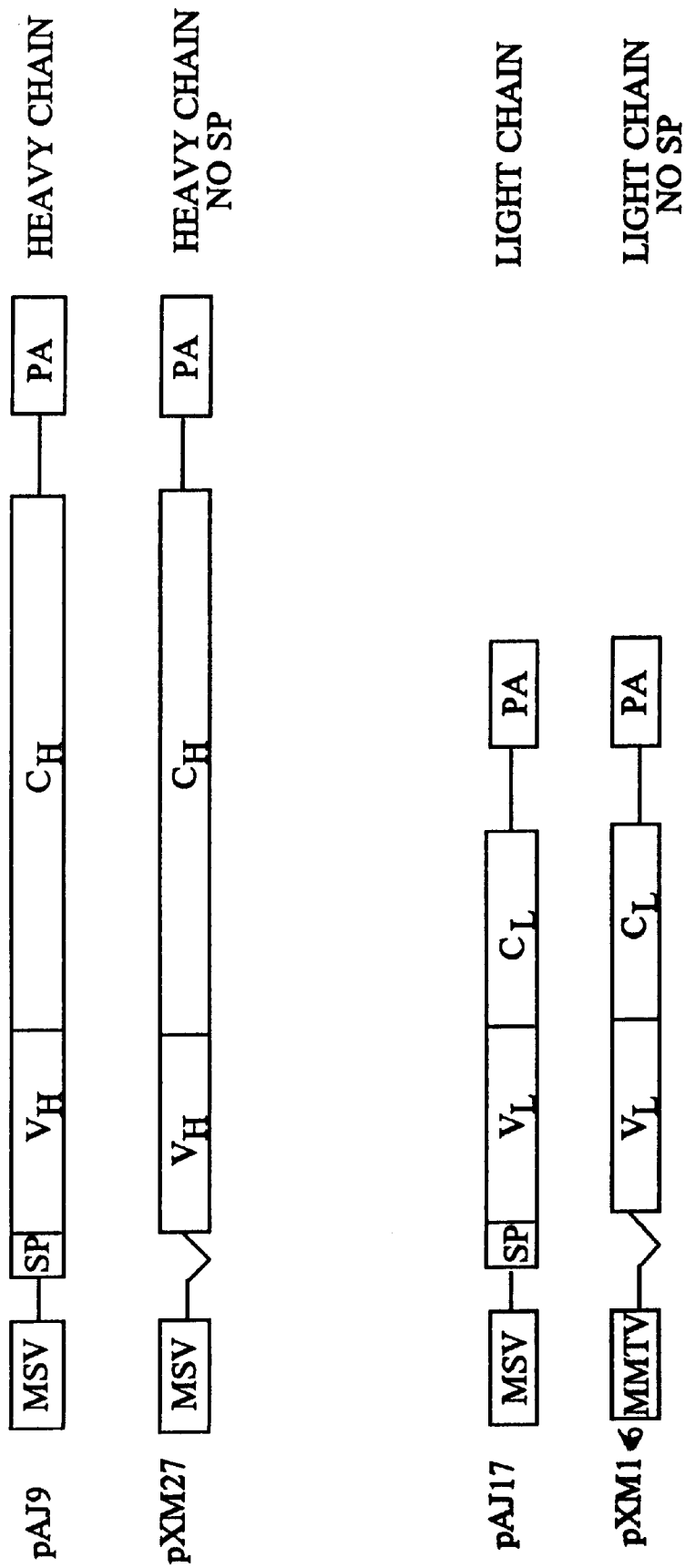
FIG. 1: Diagram showing plasmids coding for the heavy and light chains of the Y13-259 monoclonal antibody, with and without the signal peptide.

The present invention concerns a method for inactivating the function of a protein comprising:

(a) introducing one or more recombinant DNA molecules encoding an antibody or fragment thereof which specifically binds the protein into a cell (e.g., a mammalian cell) which contains the protein;

(b) expressing the recombinant DNA molecules encoding the antibody or fragment thereof intracellularly;

(c) allowing the antibody or fragment thereof to specifically bind the protein so that the function of the protein is inactivated.

Preferably, the rotein is encoded by an oncogene such as Ha-ras P-ras or K-ras. Also preferred is a method in which the protein is p21 ras protein. Further preferred is a method in which the recombinant DNA molecules are expression vectors. Additionally preferred is a method in which the antibody is a monoclonal antibody or fragment thereof. Also preferred is a method in which the signal peptide sequences have been deleted from the antibody. Further preferred is a method in which the cells are neoplastic or transformed cells. Additionally preferred is a method in which the neoplastic cells or transformed cells are converted from a transformed phenotype to a non-transformed phenotype.

As used in the present application, the term "neoplastic cells" is intended to refer to rapidly dividing cells. For the purposes of this invention, the term neoplastic cells includes cells of tumors, neoplasms, carcinomas, sarcomas, leukemias, lymphomas and the like.

As used in the present application, the term "transformed cells" means cells that divide faster than normal cells, have a fusiform phenotype, are refractile and have the capacity to form clusters rather than monolayers.

In order to practice the methods of the present invention, it is first necessary to isolate DNA sequences coding for an antibody (e.g., a monoclonal antibody) or fragment thereof (e.g., Fab, Fab', F(ab')$_2$, or Fv fragments) which is capable of specifically binding the protein of interest. Such DNA sequences can be obtained using various methods well-known to those of ordinary skill in the art. At least three alternative principal methods may be employed:

(1) the isolation of a double-stranded DNA sequence from genomic DNA or complementary DNA (cDNA) which contains the sequence;

(2) the chemical synthesis of the DNA sequence; and (3) the synthesis of the DNA sequence by polymerase chain reaction (PCR).

In the first approach, a genomic or cDNA library is created and screened in order to identify a DNA sequence coding for the desired antibody. For example, a cDNA library can be obtained using standard techniques by isolating poly A selected RNA from a hybridoma expressing the antibody of interest, reverse transcribing the RNA to create cDNA molecules, and inserting the cDNA molecules into an appropriate cloning vector (e.g., λGT10) to create the cDNA library. Various techniques can then be used to screen the genomic DNA or cDNA libraries.

For example, labeled single stranded DNA probe sequences duplicating a sequence present in the target genomic DNA or cDNA coding for the antibody of interest can be employed in DNA/DNA hybridization procedures carried out on cloned copies of the genomic DNA or cDNA which have been denatured to single stranded form.

A genomic DNA or cDNA library can also be screened for a genomic DNA or cDNA coding for an antibody or fragment thereof using immunoblotting techniques.

In one typical screening method suitable for either immunoblotting or hybridization techniques, the cDNA library, which is usually contained in a vector such as λGT10, or the genomic library is first spread out on agarose plates, and then the clones are transferred to filter membranes, for example, nitrocellulose membranes. A DNA probe can then be hybridized, assuming that at least part of the DNA sequence is known, to the clones to identify those clones containing the genomic DNA or cDNA coding for the antibody of interest.

In the second approach, the DNA sequence coding for the antibody or antibody fragment of interest can be chemically synthesized. For example, the DNA sequence coding for the antibody or antibody fragment of interest can be synthesized as a series of 100 base oligonucleotides that can then be sequentially ligated (via appropriate terminal restriction sites) so as to form the correct linear sequence of nucleotides.

In the third approach, assuming that at least part of the DNA sequence is known, the DNA sequence coding for the antibody or antibody fragment of interest can be synthesized using PCR. Briefly, pairs of synthetic DNA oligonucleotides about 30 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, U.S. Pat. Nos. 4,683,195 and 4,683,202.

It should be understood that the DNA sequence coding for the antibody or antibody fragment of interest can also be modified (i.e., mutated) to prepare various mutations. Such mutations may be either degenerate, i.e., the mutation does not change the amino acid sequence encoded by the mutated codon, or non-degenerate, i.e., the mutation changes the amino acid sequence encoded by the mutated codon. These modified DNA sequences may be prepared, for example, by mutating the DNA sequence coding for the monoclonal antibody of interest so that the mutation results in the deletion, substitution, insertion, inversion or addition of one or more amino acids in the encoded polypeptide using various methods known in the art. For example, the methods of site-directed mutagenesis described in Taylor, J. W. et al., Nucl. Acids Res. 13, 8749–8764 (1985) and Kunkel, J. A., Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). Both degenerate and non-degenerate mutations may be advantageous in producing or using the polypeptides of the present invention. For example, these mutations may permit higher levels of production, easier purification, or provide additional restriction endonuclease recognition sites. A particularly advantageous mutation involves removal of the signal peptides from the chains of the antibody so that the resulting antibody fragment cannot be secreted from the cell in which it is to be expressed. All such modified DNAs (and the encoded polypeptide molecules) are included within the scope of the present invention.

As used in the present application, the term "modified", when referring to a nucleotide or polypeptide sequence, means a nucleotide or polypeptide sequence which differs from the wild-type sequence found in nature.

Once the DNA sequence encoding the monoclonal antibody of interest has been isolated, it may be inserted into an appropriate expression vector. Expression vectors of utility in the present invention are often in the form of "plasmids", which refer to circular double stranded DNAs which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front of (i.e., upstream of) the DNA sequence and followed by the DNA sequence coding for the antibody of interest, transcription termination sequences and the remaining vector. The expression vectors may also include other DNA sequences known in the art, for example, stability leader sequences which provide for stability of the expression product, sequences which allow expression of the structural gene to be modulated (e.g., by the presence or absence of nutrients or other inducers in the growth medium), marking sequences which are capable of providing phenotypic selection in transformed host cells, and sequences which provide sites for cleavage by restriction endonucleases. The characteristics of the actual expression vector used must be compatible with the cell into which the expression vector is to be inserted. For example, if the expression vector is to be inserted into a particular type of neoplastic cell, the expression vector should contain a promoter which allows expression in this cell type. Suitable promoters include, for example, the long terminal repeats of the Moloney sarcoma virus, the Rous sarcoma virus and the mouse mammary tumor virus, as well as the early regions of Simian virus 40 and the polyoma virus. As selectable markers, the bacterial genes encoding resistance to the antibodies neomycin and G418 (neo) puromycin (pur) or hygromycin (hygro), or mammalian genes encoding thymidine kinase can be employed. All of these materials are known in the art and are commercially available.

Suitable expression vectors containing the desired coding and control sequences may be constructed using standard recombinant DNA techniques known in the art, many of which are described in Maniatis, T. et al., *Molecular Cloning: A Laboratory Manual*, Cold Spring Harbor Laboratory, Cold Spring Harbor, N.Y. (1982).

Once expression vectors containing the DNA sequence coding for the monoclonal antibody of interest have been created, they may be introduced into cells (both in vivo and in vitro) which express the corresponding antigen in order to inactivate the function of the antigen. Expression vectors may be introduced into these cells by various methods known in the art. For example, transfection of cells with expression vectors can be carried out by the calcium phosphate precipitation method. However, other methods for introducing expression vectors into cells, for example, electroporation, biolistic fusion, liposomal fusion, nuclear injection and viral or phage infection can also be employed.

Retroviral vectors would be particularly advantageous expression vectors in the practice of the methods of the present invention. Retroviral viral vectors can only integrate into the genome of dividing cells as single copies, and therefor provide a useful vehicle for selective targeting of neoplastic cells. Retroviral vectors offer further advantage, since they have no limitations in host range, as evidenced by their ability to successfully infect many different cell types. For example, see Cepko, C. in *Neuromethods*, Vol. 16, pp. 177–218, Clifton, N.J., The Humana Press, Inc. (1989); Gilboa, E., BioEssay, 5(6), 252–257 (1987); Friedmann, T., Science 244, 1775–1781 (1989); Shih et al. in Vaccines 85, Cold Spring Harbor Press, Cold Spring Harbor, N.Y. (1985), pp. 177–180; Varmus, H., Science 240, 1427–1435 (1988). Foreign genes and promoter elements can be inserted into plasmid DNA equivalents of the retroviral genome, which retain the packaging signal, psi. These plasmids are then transfected into packaging cell lines, which carry wild-type retroviral sequences lacking the psi element needed for packaging of their own RNA into virion particles (Cone, R. D. et al., Proc. Natl. Acad. Sci. USA 81:6349–6353 (1984); Miller, A. D. et al., Mol. Cell. Biol. 6:2895–2902 (1986); Mann, R. et al., Cell 33:153–159 (1983)). The packaging line can insert the psi-bearing RNA encoded in the foreign gene-bearing retrovirus sequences into virion particles. These lines then release into the medium only replication-defective virions containing foreign gene sequences and no replication competent virions. These replication-deficient virions can efficiently infect other dividing cells and insert the foreign genes into their genome.

Generally, methods are known in the art for the in vivo and in vitro infection of the cells using retroviral vectors. For example, in order to infect neoplastic cells in vivo, the virus is typically injected into the host at or near the site of neoplastic growth. For the most part, the virus is provided in a therapeutically effective amount to infect the target cells.

Herpes simplex virus type 1 (HSV-1) mutants with deletions in one or more genes necessary for viral replication can also be used for the in vivo and in vitro delivery of DNA sequences coding for antibodies or fragments thereof to target cells. In this case, the DNA sequences coding for antibodies or fragments thereof are inserted into the mutated HSV-1 viral genome operably linked to and under the control of a promoter sequence which allows the DNA sequence to be expessed in the target cells. The resulting virus can then be used to infect the target cells. For example, in order to infect neoplastic cells in vivo, the virus is injected at or near the site of neoplastic growth in order to introduce the DNA sequences coding for antibodies or fragments thereof into the neoplastic cells [See, Longnecker, R. et al in Viral Vectors, Current Communications in Molecular Biology, Cold Spring Harbor Press, p. 68 (1988)].

It should be recognized that the DNA sequence coding for an antibody or fragment thereof may be targeted to specific cell types using, for example, viral promoters or cell or tumor specific promoters.

It should, of course, also be understood that not all expression vectors and DNA regulatory sequences will function equally well to express the DNA sequences coding for monoclonal antibodies. However, one of ordinary skill in the art may make a selection among expression vectors and DNA regulatory sequences using the guidance provided herein without undue experimentation and without departing from the scope of the present invention.

The methodology of the present invention can also be employed to detect the biological function of other genes within the cell. For example, by blocking the function of a protein encoded by a gene, it may be possible to turn on or off the expression of other genes which are either housekeeping genes or genes involved in functions downstream of the function of the gene being blocked (i.e., genes involved in cascade reactions). These genes can be studied using subtraction cDNA libraries from cells in which the gene function has been blocked versus cells in which it has not.

The methodology of the present invention can also be used in studies of the phenomenon of differentiation, in which a protein can be blocked in a way that can trigger constitutive induction of differentiation and even proliferation. Similarly, by blocking a protein function it will be possible to render the cells undifferentiated, even in the presence of agents that can induce these changes.

The following example is further illustrative of the present invention. This example is not intended to limit the scope of the present invention, and provides further understanding of the invention.

EXAMPLE 1

I. Materials and Methods

A. Cell lines

NIH3T3 cells and NIH3T3 cells transformed by activated Ha-ras (44-9-1-1) [Santos, E. et al., Nature 298, 343–347 (1982)], K-ras (K-NIH) [Notario, V. et al., Cancer Cells, pp. 425–432, Oncogen and Viral Genes, Cold Spring Harbor Laboratory (1984)] or by the amplified non-mutated Ha-ras allele (115-6-2-1) [Pulciani, S. et al., Mol. Cell. Biol. 5, 2836–2841 (1985)] were maintained in Dulbecco's Modified Eagle's Medium (DMEM) supplemented with 10% calf serum (CS) (Colorado Serum Company), 10 U/ml of penicillin, and 10 U/ml of streptomycin (Gibco). The cells were kept at 37° C. and 7% $CO_2$ concentration.

B. Transfections

NIH3T3 cells or NIH3T3 cells transformed by the different activated ras alleles were transfected with 1 μg of test plasmid DNA and 100 μg of pSV2 neo [See, Southern, P. and Berg, P., J. Mol. Appl. Genet. 1, 327–331 (1982)] or pHygro [See, Sugden, M. et al., Mol. Cell. Biol. 5, 410–413 (1985)] (unless stated otherwise herein) by the calcium phosphate precipitation technique [Graham and Van der Eb, Virology 52, 456–467 (1973)].

Transfectants were selected with DMEM containing 10% CS and 500 μg/ml of G418 or 150 μg/ml of Hygromycin B. Colonies were scored and picked after 14 days of transfection.

C. Isolation of cDNA Clones

The cDNA from the hybridoma cell line producing Y13-259 monoclonal antibody [ATCC # CRL 1742] was prepared from a third cycle poly A selected RNA using a cDNA synthesis system (Amersham). A cDNA library was prepared in λgt 10 using a cloning system obtained from Amersham. One million phage were screened under stringent conditions using $^{32}$p labeled nick-translated probes. In order to screen for the light chain, a rat pstI C κ cDNA probe of 500 bp was used. In the case of the heavy chain, mouse cγ2a 2.3 kb and 2.0 kb EcoRI and MstII probes were employed.

D. Expression Plasmids DNA inserts isolated from 30 plaque purified κ cDNAs ranged in size from 0.9 kb to 1.6 kb and those isolated from 21 plaque purified γ2a cDNAs ranged from 1.4 kb to 1.7 kb. The inserts were assayed for expression by subcloning into the unique Eco RI site of pMEX or pMEX neo. pMEX and pMEX neo are mammalian expression vectors in which the polylinker sequence of pUC 118 (without the Hind III recognition site) is flanked by the Moloney murine sarcoma virus (MSV) long terminal repeat (LTR) and the polyadenylation site of SV40. Two expression plasmids were isolated that expressed the heavy and light chains of the correct molecular weight; these were designated pAJ9 and pAJ17, respectively.

The heavy and light chains cDNAs were subcloned into pUC118, a pUC19 derived vector, and were sequenced. The sequence of each gene was matched to the sequence of the murine γ1 [Honjo, T. et al., Cell 18 559–568 (1979)] and the murine Balb/c γ2a heavy chain [Sikorav, J. L., Nucl. Acids Res. 8, 3143–3155) (1980)] and the murine MPC-11 κ chain [Burstein, Y. and Schechter, I., Biochemistry 17, 2392–2400 (1978)] and the murine MAK 33 κ chain [Buckel P. et al., Gene 51, 13–19 (1987)]. The signal peptide of both heavy and light chains was removed by standard molecular biology techniques. In the case of the heavy chain two oligonucleotides were made; a 40 bp oligonucleotide was created containing a BamHI site, the Kosak's ribosomal attachment concensus sequence, [Kosak, M., Nucl. Acids Res. 12, 857–872 (1984)] followed by an initiator methionine and 9 amino acids coded by the heavy chain gene. The second oligonucleotide had 33 bp and contained the EcoRI site at the far 3' end followed by a stop codon and 8 amino acids. Both oligonucleotides were designed in order to be able to anneal complementary strands at opposite ends of the heavy chain template. Polymerase chain reaction was carried out with these oligonucleotides, and the product was cloned into the BamHI/EcoRI sites of pMEX and sequenced. The clone that had the correct sequence was named pXM27 and used for protein expression. In the case of the light chain, a new Aat II restriction site was created immediately downstream from the signal peptide sequence by site directed mutagenesis [Kunkel, J. A., Proc. Natl. Acad. Sci. U.S.A. 82, 482–492 (1985)]. The signal peptide sequence contained within the BamHI and the AatII sites was removed and replaced by a double stranded oligonucleotide containing a BamHI site, the Kosak's ribosomal attachment sequence, a starting methionine and 3 amino acids present in the light chain immediately after the signal peptide. The light chain was subcloned under the control of the mouse mammary tumor virus (MMTV) promoter; the resulting plasmid was designated pXM16 and used for protein expression.

E. Immunoprecipitations

For immunoprecipitations of ras proteins and/or the heavy and light chains of the Y13-259 monoclonal antibody, 100 mm plates of 80% confluent cells were metabolically labeled for 3½ hours at 37° C. with 1.5 ml of $^{35}$S methionine and cysteine (translabel ICN) as 200 μCi/ml of medium. Cells were rinsed twice with phosphate buffered saline (PBS). Cells were lysed at 4° C. in EBC buffer (50 mM Tris HCl pH 8.0, 120 mM NaCl, 0.5% Nonidet P-40). The cell extracts were spun for 5 minutes; the supernatant was mixed with the primary antibody and then it was incubated for 1 to 2 hours at 4° C. 50 μl of Protein A Sepharose beads (Pharmacia) resuspended in NET N containing 1 mg/ml bovine serum albumin (BSA) was added and incubated for 30 minutes at 4° C. The beads were washed twice with NET N (20 mM Tris HCl (pH 8), 100 mM NaCl, 1 mM EDTA and 0.5% Nonidet P-40) containing 0.5 M LiCl and once in NET N alone. The immunoprecipitates were boiled in sample buffer (62.5 μM Tris HCl (pH 6.8), 10% glycerol and 0.1 M dithiothreitol) and analyzed by sodium dodecyl sulphate polyacrylamide gel electrophoresis (SDS PAGE).

F. ELISA

Unlabeled mouse anti rat chain κ (AMAC Labs) was bound to PVC plates at a concentration of 1 μg/well diluted in PBS. The plates were incubated for 3 hours at room temperature. The mix was discarded and the plates were incubated overnight at 4° C. with 0.1% BSA dissolved in PBS.

Cell extracts were prepared by lysing cells in EBC buffer containing 0.1% Nonidet P-40 for 2 minutes at room temperature. The lysates were spun for 5 minutes at 4° C. and the protein concentration of the supernatants was obtained using a protein assay kit (Biorad). Cell extracts of known protein concentration were added to the plates and incubated for 3 hours at 4° C. The supernatants were discarded and the plates were washed 4 times with PBS containing 0.05% Tween. A horseradish peroxidase conjugated antibody against rat heavy and light chains (Dako) previously diluted 1/200 in PBS containing 5% FCS was then added. The plates were incubated for 2 hours at 4° C., and were then washed 4 times in PBS containing 0.05% Tween and the color reaction was developed by using a TMB microwell peroxidase substrate system (Kirkegaard and Perry) and read in a Titertek plate reader.

G. Immunofluorescence

Cover slips with cells were washed twice with PBS and fixed in 50% acetone diluted in methanol, and were then washed again twice in PBS and incubated for 1 hour at room temperature with rabbit anti murine Golgi Apparatus (obtained from Dr. Brian Burke, Harvard University) previously diluted 1/100 in PBS containing 3% fetal calf serum. The cover slips were rinsed twice in PBS and incubated with donkey anti rabbit biotinylated conjugated antibodies (Amersham) or goat anti rat fluorescein conjugated antibodies (Dako) for ½ hour at room temperature (the antibodies were previously diluted 1/500 in PBS containing 3% fetal calf serum). Finally, the coverslips were rinsed twice in PBS and/or incubated for ½ hour at room temperature with streptavidin conjugated with Texas red (Amersham), then were rinsed once with PBS, mounted and viewed under the microscope.

II. RESULTS

A. Isolation of cDNA Clones

Poly A selected RNA isolated from the hybridoma cells expressing Y13-259 monoclonal antibody was used to prepare a $10^6$ phage member Eco R1 cDNA library in the $\lambda$GT10 cloning vector. This library was screened for the light chain with a 500 bp psTICκ rat probe and for the heavy chain with a 2.3 Kb and 2.0 Kb EcoR1 and MST II $\gamma^{2a}$ mouse probes. 30 recombinant phage were picked with the Cκ probe with inserts that ranged from 0.9 Kb to 1.6 Kb in size, and 21 phage were picked with the Cγ2a probes with inserts that ranged from 1.4 Kb to 1.7 Kb in size.

The inserts were assayed for expression by subcloning into the unique EcoRI site of pMEX or pMEX neo, which are mammalian expression vectors that carry a multiple cloning site flanked by a Moloney murine sarcoma virus (MSV) long terminal repeat (LTR) and polyadenylation signal from SV 40. Two expression plasmids that produced the heavy and light chain proteins of the correct molecular weight were obtained and designated pAJ9 and pAJ17 respectively. (FIG. 1).

The heavy and light chain genes of Y13-259 monoclonal antibody were subsequently subcloned into the EcoRI site of the pUC 118 vector and were sequenced. The nucleotide sequence of the light chain is shown in SEQ ID NO:1 and the deduced amino acid sequence of the light chain is shown in SEQ ID NO:2. The signal peptide sequence of the light chain (amino acids 1–20 in SEQ ID NO:2) is encoded by nucleotides 1 to 60 in SEQ ID NO:1. The partial nucleotide sequence (5') of the heavy chain is shown in SEQ ID NO:3 and the partial deduced amino acid sequence (N terminus) of the heavy chain is shown in SEQ ID NO:4. The signal peptide sequence of the heavy chain (amino acids 1–20 in SEQ ID NO:4) is encoded by nucleotides 1–60 in SEQ ID NO:3. The sequence of each gene was matched to the sequence of the murine MPC-11 κ chain [Burstein, Y. and Schechter, I., Biochemistry 17, 2392–2400 (1978)], the murine MAK 33 κ chain [Buckel, P. et al. Gene 51, 13–19 (1987)] and the murine $\gamma_1$, and murine Balb/c $\gamma_2$a heavy chains (Honjo, T. et al., Cell 18, 559–568 (1979); Sikorav, J. L., Nucl. Acids Res. 8, 3143–3155 (1980)].

The signal peptide of both heavy and light chains was removed as follows: In the case of the heavy chain, two oligonucleotides were made, a 40 bp oligonucleotide was created containing a 5' Bam HI site, the Kosak's ribosomal attachment consensus sequence [Kosak, M., Nucl. Acids Res. 12, 857–872 (1984)], followed by a starting methionine and 9 amino acids coded by the heavy chain. The second oligonucleotide was 33 bp and contained an EcoR1 site at the 3' end followed by a stop codon and 8 amino acids upstream of the 3' end. These oligonucleotides were able to anneal to the complementary strands and at opposite ends of the heavy chain gene. Polymerase chain reaction was carried with these oligonucleotides; the 1.5 Kb product was cloned into the BamH1/EcoRI sites of pMEX and then was sequenced. The expression vector coding for the correct sequence was designated pXM 27 (FIG. 1).

The light chain was subjected to site directed mutagenesis and a new AaT II site was created immediately downstream of the secretory signal peptide. The sequence contained within the BamHI sited found in the pMEX polylinker and the Aat II site was removed and replaced by a double stranded oligonucleotide containing at the 5' end a BamHI site followed by the Kosak ribosomal attachment consensus sequence, a starting methionine and 3 amino acids coded immediately after the signal peptide. The light chain without the signal peptide was subcloned under the control of the mouse mammary tumor virus promoter and named pXM 16 (FIG. 1).

B. Expression and assembly of monoclonal antibody Y13-259 in mouse fibroblasts

Figure 2:
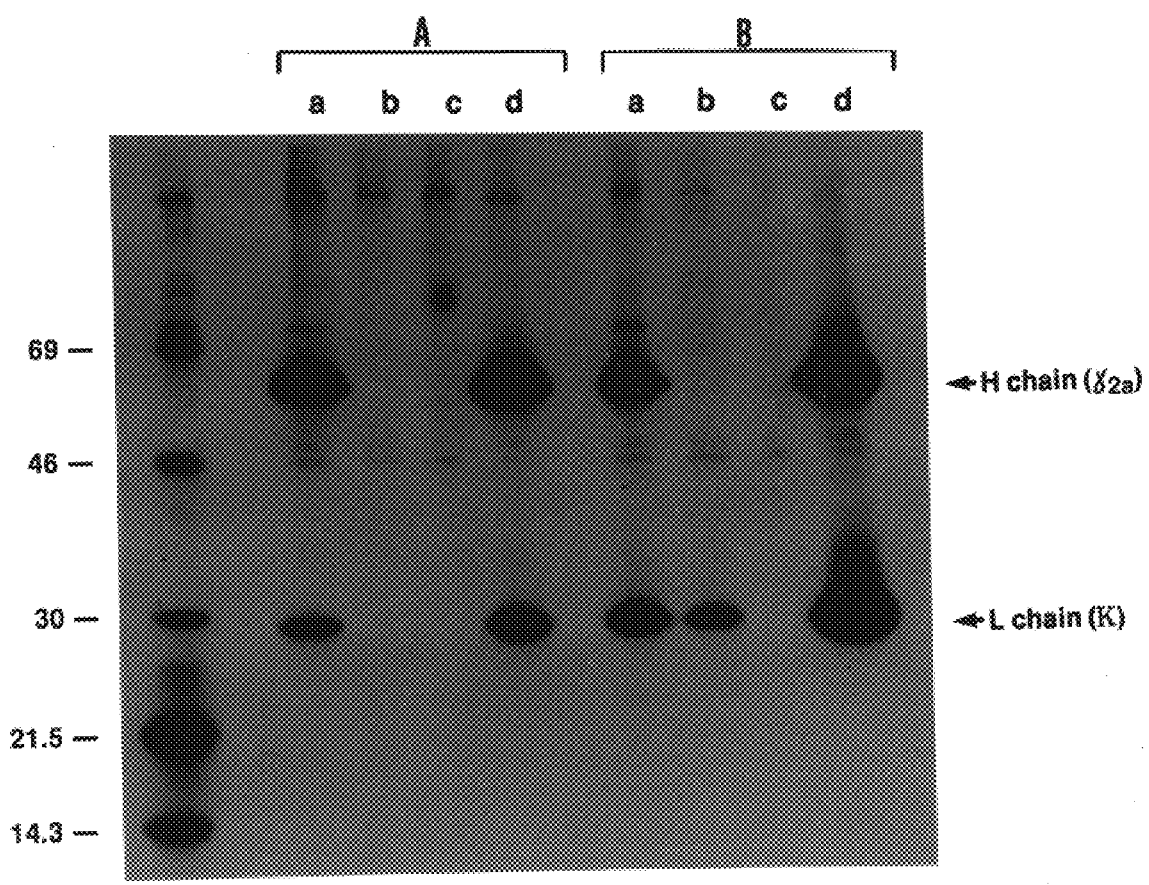
FIG. 2: Immunoprecipitation to show correct Y13-259 immunoglobulin chain assembly when expressed in E89-6-19 cells. E89-6-19 cells were labelled with $^{35}$S methionine and cysteine for 3½ hours. Extracts were made under nondenaturing conditions (see discussion herein below in materials and methods). The same number of trichloroacetic acid precipitable counts of each extract was incubated with either goat anti Fc region or rabbit anti rat serum. The immunoprecipitates were analysed by polyacrylamide gel electrophoresis (PAGE) on a 15% gel. Track a) E89-6-19 cells; track b) E65-3-7 cells; track c) NIH3T3 cells; track d) Y13-259 hybridoma cells.

To test whether the cDNAs of the heavy and light chains of the Y13-259 monoclonal antibody expressed a biologically functional antibody in mouse fibroblasts, NIH3T3 cells were cotransfected with pAJ9, the plasmid coding for the heavy chain and pHygro [Sugden, M. et al., Mol. Cell Biol. 5, 410–413 (1985)], a plasmid that confers resistance to Hygromycin B. Cells were selected in Hygromycin B containing media for a period of 14 days, and the selected cells obtained were grown and tested for heavy chain expression by immunoprecipitation analysis. The colonies that expressed the highest levels of heavy chain protein were selected and subsequently transfected with pAJ17, a plasmid that codes for the light chain and the neomycin resistance gene. Cells were selected for 14 days in G418 containing media and were tested for heavy and light chain expression by immunoprecipitation. From the cell lines obtained, the one that expressed the highest levels of heavy and light chain proteins was chosen and denominated E89-6-19. In order to observe if the proteins produced by the heavy and light chain genes of the monoclonal antibody Y13-259 are capable of being assembled into an antibody molecule, E89-6-19 cells were immunoprecipitated under non-denaturing conditions with goat anti rat Fc region antibodies. (i.e., a serum that will only recognize the assembled heavy chain proteins). As shown in FIG. 2, panel A, it is possible to observe that the light chain protein coimmunoprecipitates with the heavy chain (Track a). The same result is observed in the case of the heavy and light chains of the antibody produced by the Y13-259 hybridoma (Track d). As a positive control the heavy and light chain proteins expressed by E89-6-19 cells (Track a) and by the Y13-259 hybridoma cell line (Track b, panel B) were immunoprecipitated under nondenaturing conditions with rabbit anti rat immunoglobulins, i.e., a serum that contains antibodies that independently recognize the heavy and light chains of the antibody, and it was possible to observe the same proteins of 59 Kd and 29 Kd estimated molecular weight.

In order to test the specificity of the immunoglobulins employed to immunoprecipitate the heavy and light chain proteins of monoclonal antibody Y13-259, E65-6-7 cells (i.e., NIH3T3 cells expressing only the light chain of the monoclonal antibody Y13-259) and NIH3T3 cells were immunoprecipitated using non-denaturing conditions with goat anti rat Fc region antibodies and rabbit anti rat antibodies. It was found that only the rabbit anti rat antibodies can recognize the light chain proteins expressed in E65-6-7 cells (Track b, panel B) whereas the anti Fc region antibodies do not (Track b, panel A). Both types of sera do not recognize any type of background proteins in NIH 3T3 cells alone (Tracks c in panels A and B). This experiment, therefore, clearly shows that the anti Fc region antibodies are detecting an associated heavy and light chain of the monoclonal antibody Y13-259.

C. Recognition of ras by monoclonal antibody Y13-259 produced in E89-6-19 cells

Figure 3:
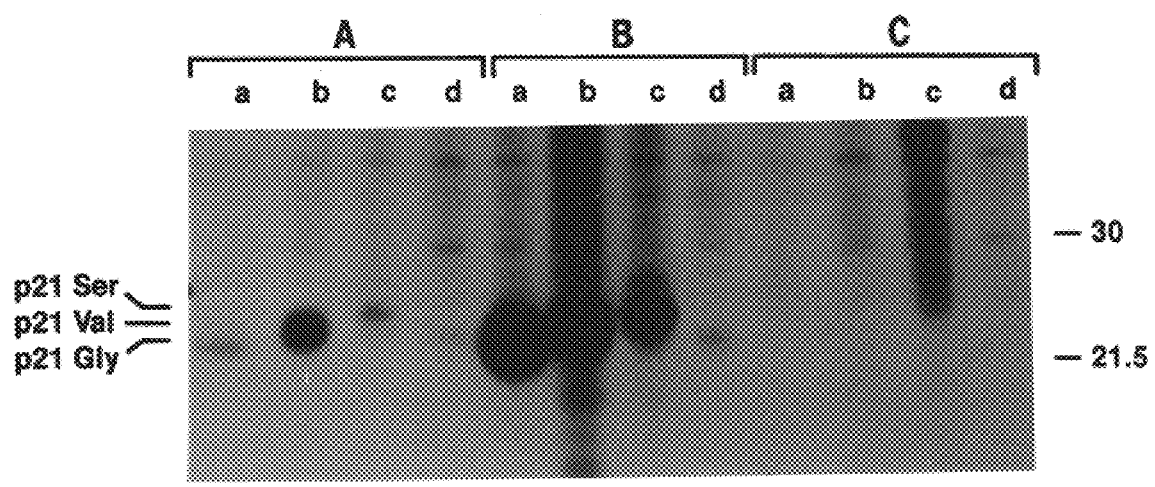
FIG. 3: Detection of p21 ras protein by Y13-259 monoclonal antibody produced in E89-6-19 cells. Cells were labelled with $^{35}$S methionine and cysteine for 3½ hours. Extracts of 115-6-2-1 cells expressing ras with GLY at position 12 track a), 44-9-1-1 cells expressing ras with VAL at position 12 track b), K-NIH cells expressing ras with SER at position 12 track c), NIH3T3 cells track d), were made under nondenaturing conditions (see discussion herein below in materials and methods). These were incubated with extracts of E89-6-19 cells (cell extracts prepared under nondenaturing conditions) panel A, with 2 µg of purified Y13-259 monoclonal antibody panel B, and extracts of NIH3T3 cells (cell extracts prepared under nondenaturing conditions) panel C. The immunoprecipitates were analysed by PAGE on a 15% gel.

In order to observe if the antibody produced in E89-6-19 cells has the capacity to recognize p21 ras, cell extracts of E89-6-19 cells were prepared under nondenaturing conditions and used to precipitate $^{35}S$ methionine and cysteine labelled cell extracts of 44-9-1-1 cells, which are NIH3T3 cells transformed by an activated Ha-ras gene which express a p21 protein with valine at position 12, K-NIH, which are NIH3T3-cells transformed by K-ras and express a p21 protein with serine at position 12, and 115-6-2-1 cells, which are NIH 3T3 cells transformed by the amplified unactivated Ha-ras allele which express a p21 protein with glycine at position 12 and NIH3T3 cells. FIG. 3, panel A shows the results of this experiment. It can be observed that the antibody expressed by E89-6-19 cells can recognize p21 with glycine at position 12 (Track a), valine at position 12 (Track b), and serine at position 12 (Track c) and low levels of non activated P21 with glycine at position 12 in NIH3T3 cells.

As a positive control the cell extracts of the cell lines described above were also immunoprecipitated with hybridoma purified Y13-259 antibodies and it can be observed (panel B) that the same proteins recognized by the monoclonal antibody Y13-259 produced in E89-6-19 cells can also be detected by the purified antibody. When NIH3T3 cell extracts were employed to carry out immunoprecipitations of the cell extracts (panel C), it was not possible to detect any proteins of the size of those expressed by the different ras alleles.

D. Endogenous recognition of p21 ras protein with glycosylated and non-glycosylated heavy chain protein of monoclonal antibody Y13-259 produced in E89-6-19 cells It has been shown that antibody heavy chain glycosylation plays an important role during antibody antigen recognition. This effect has been shown to be due to changes in protein configuration which in turn are due to the lack of carbohydrate groups [Olden, K. et al., Biochem. Biophys. Acta 650, 209–232 (1982)].

To test whether the absence of glycosylation might interfere with the recognition of Y13-259 antibodies produced in non myeloid cells, antibody antigen recognition was examined in the presence and absence of tunicamycin, which prevents N-linked glycosylation of all cell glycoproteins.

Figure 4:
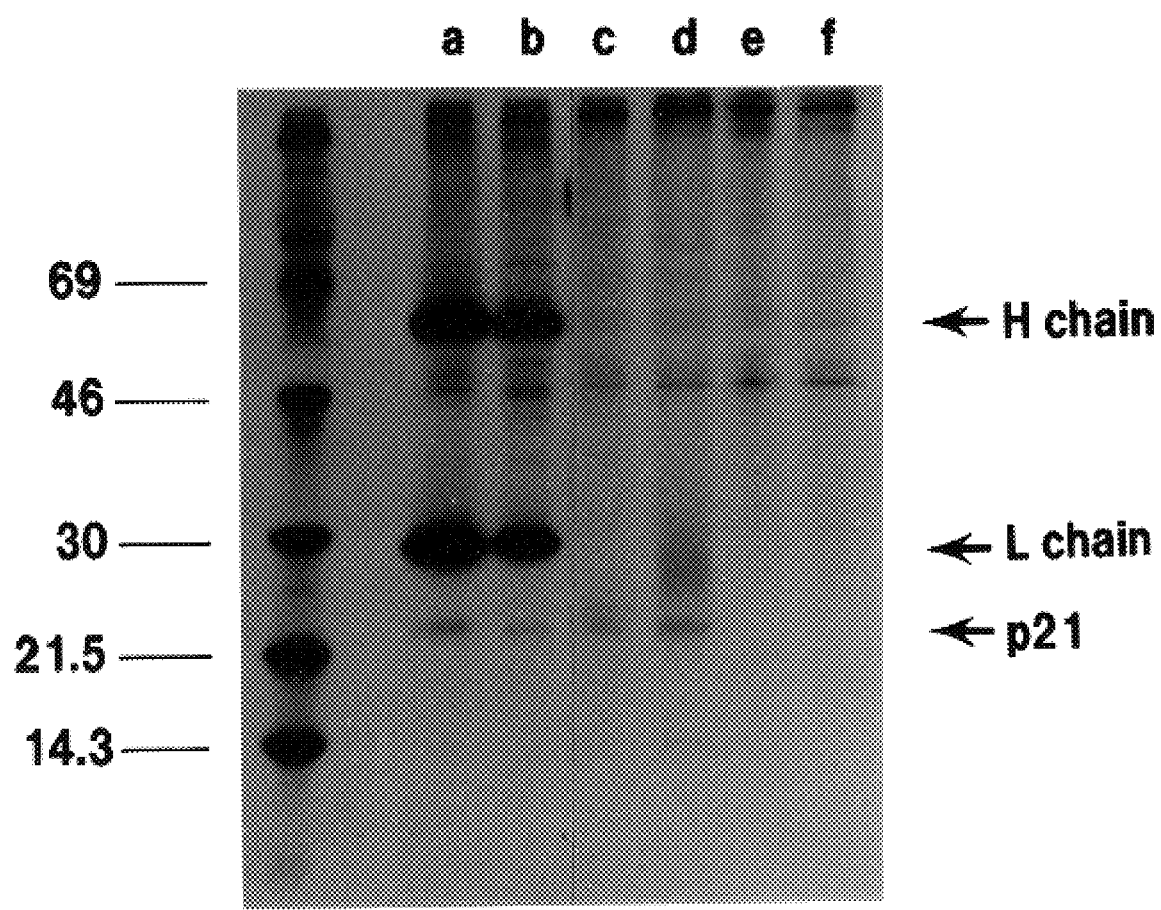
FIG. 4: Endogenous immunoprecipitation of p21 ras by Y13-259 monoclonal antibody expressed in E89-6-19 cells. Cells were labelled with $^{35}$S methionine and cysteine for 3½ hours. Extracts were made in nondenaturing conditions (see discussion herein below in materials and methods), and immunoprecipitated as follows: tracks a) and b) E89-6-19 with rabbit anti rat serum; tracks c) and d) 115-6-2-1 cells with 0.5 µg of hybridoma purified Y13-259 monoclonal antibody; tracks e) and f) NIH3T3 cells with rabbit anti rat serum. The immunoprecipitates were analysed by PAGE in a 15% gel.

E89-6-19 cells were labelled with $^{35}S$ methionine and cysteine in the absence and presence of 10 µg/ml tunicamycin for 3½ hours. Cells were lysed under nondenaturing conditions and immunoprecipitated with rabbit anti rat immunoglobulins. As noted in FIG. 4, it was observed that the heavy and light chains of the monoclonal antibody Y13-259 coimmunoprecipitate a protein of 21 kd molecular weight in the absence and presence of tunicamycin treatment (Tracks a and b). It was also observed that the protein coimmunoprecipitated by the Y13-259 antibody produced in E89-6-19 cells is of the same molecular weight as the one detected by the hybridoma purified Y13-259 from immunoprecipitates of 115-6-2-1 cell extract untreated and treated with tunicamycin (Tracks c and d). A protein of this molecular weight was not observed when rabbit anti rat serum was employed to immunoprecipitate NIH3T3 cell extracts untreated and treated with tunicamycin (Tracks d and e).

In order to prove that the coimmunoprecipitated protein was ras, the experiment described above was carried out in duplicate; the proteins of the second gel were transferred to nitrocellulose and subjected to western blotting. The blot was stained after incubation with a pantropic anti ras antibody and the same protein of 21 kd coimmunoprecipitated by the monoclonal antibody Y13-259 was detected by this procedure (data not shown), indicating that Y13-259 produced in E89-6-19 cells can recognize endogenous ras.

E. Secretion of the monoclonal antibody Y13-259 from E89-6-19 cells

The secretion of immunoglobulins by transfected genes into cells of non-lymphoid origin has been demonstrated [Cattane, A. and Neuberger, M. EMBO J. 6, 2753 (1987)]. This effect was also tested in E89-6-19 cells.

Figure 5:
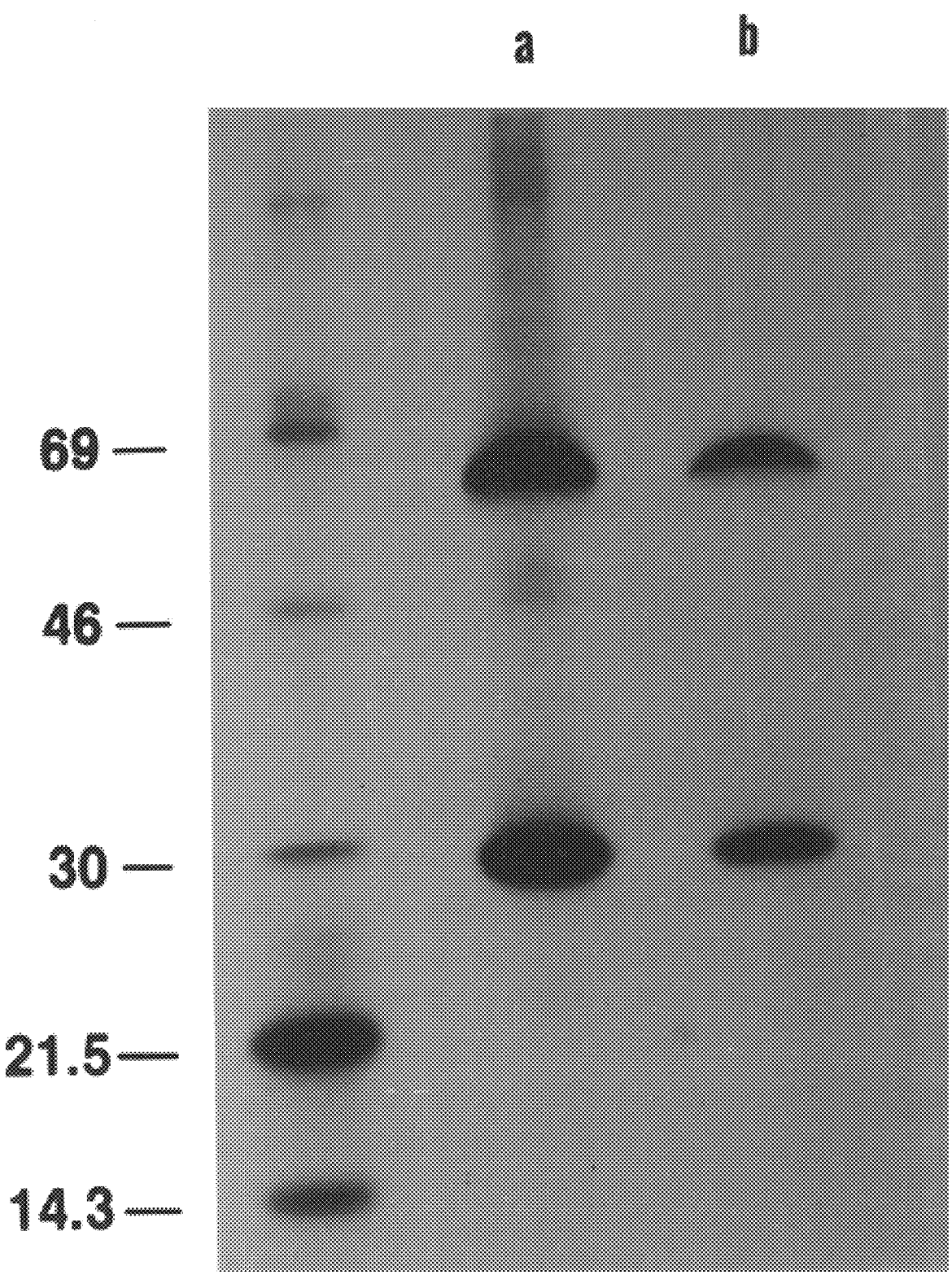
FIG. 5: Secretion of monoclonal antibody Y13-259 from E89-6-19 cells. E89-6-19 cells expressing the Y13-259 monoclonal antibody were labelled for 6 hours with $^{35}$S methionine and cysteine in serum free medium. Cell extracts were prepared under nondenaturing conditions (see discussion herein below in materials and methods), and the same number of trichloroacetic acid precipitable counts from the cell extract and from the medium were immunoprecipitated under nondenaturing conditions with rabbit anti rat immunoglobulins. The immunoprecipitates were analysed by PAGE on a 15% gel. Track a) E89-6-19 cells, Track b) Media of E89-6-19 cells

E89-6-19 cells were seeded in serum free media supplemented with growth factors. After 24 hours, they were labelled for 6 hours with $^{35}S$ methionine and cysteine. Cell extracts were made under nondenaturing conditions. Cell extracts and growing media were immunoprecipitated. FIG. 5 shows that the antibody becomes secreted into the media (Track b) and that the amount secreted is 50% of that produced by the cells.

F. Cellular localization of the monoclonal antibody Y13-259 in E89-6-19 cells

Figure 6A:
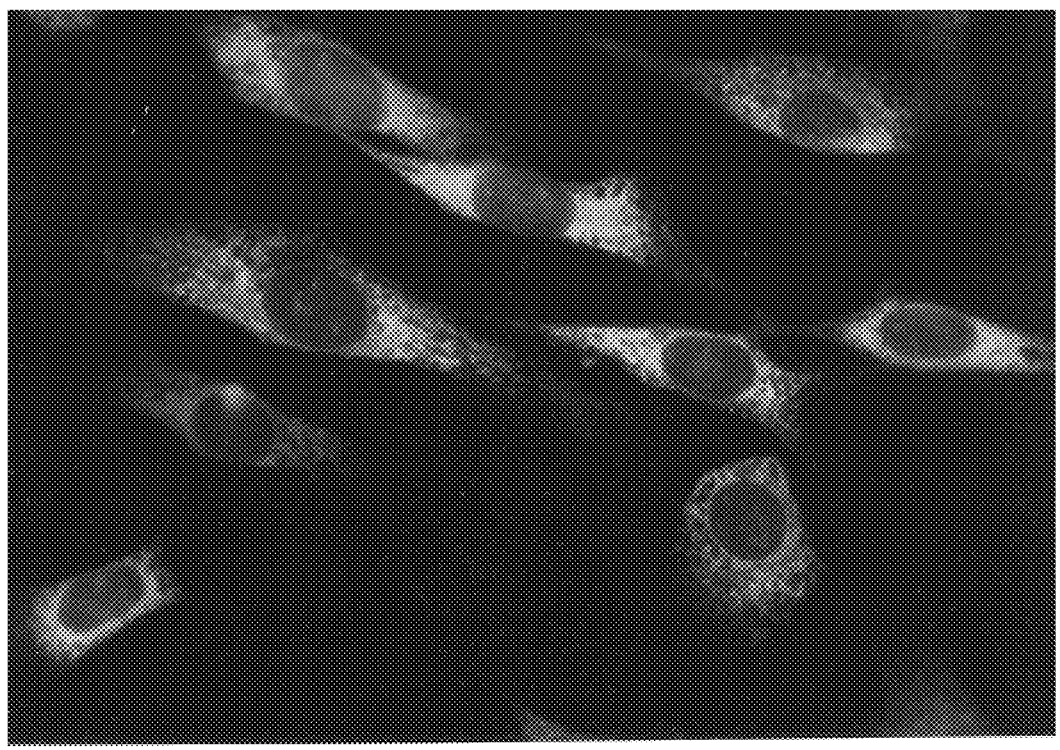
FIG. 6: Cellular localization of the monoclonal antibody Y13-259 expressed in E89-6-19 cells. Cells were fixed and stained as indicated herein below in materials and methods. a) E89-6-19 cells stained for the presence of Y13-259 monoclonal antibody, b) E89-6-19 cells stained for the presence of the golgi apparatus.
Figure 6B:
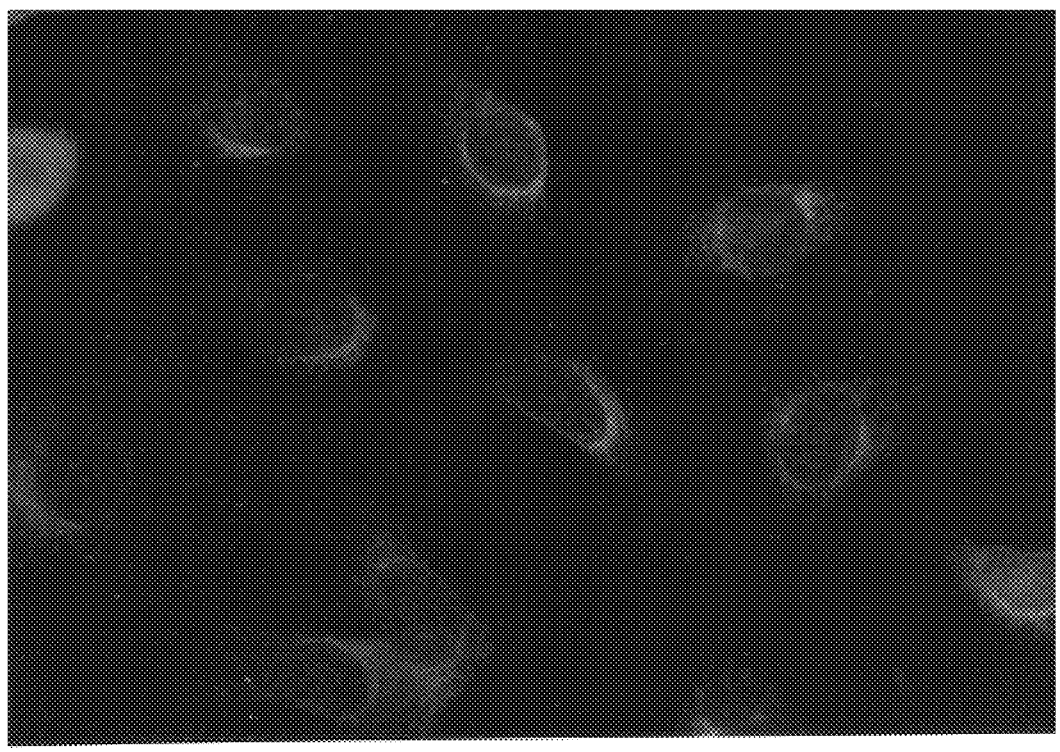

The expression and localization of the monoclonal antibody Y13-259 in E89-6-19 cells was detected by immunofluorescence using anti rat antibodies as described in Materials and Methods. It was possible to observe that, as expected, the antibody is localized within the organelles involved in the protein secretory pathway (FIG. 6, A) and if the pattern is compared to that of the golgi apparatus (FIG. 6, B), a clear correlation in distribution can be seen. It can be concluded from the above that the monoclonal antibody Y13-259, when produced in mouse fibroblasts, has the same biological and functional characteristics as the one produced by the myeloid cell line.

It is important to indicate that the experiments described above were also carried out in 44-9-1-1 cells. The antibody showed the same characteristics as when it was synthesized in E89-6-19 cells. However, the transformed cells did not show any changes in morphology, which was expected in view of the fact that both the heavy and the light chain genes do code for the secretory signal peptide.

G. Transfection and expression of the heavy chain of monoclonal antibody Y13-259 without the secretory signal peptide The aim of this study was to block ras endogenous activity by the biological action of a functional antibody. In order to render the antibody accessible to membrane bound ras, the signal peptide of both heavy and light chain genes was removed, as described previously, in such a way as to express a cytoplasmic antibody.

Figure 7:
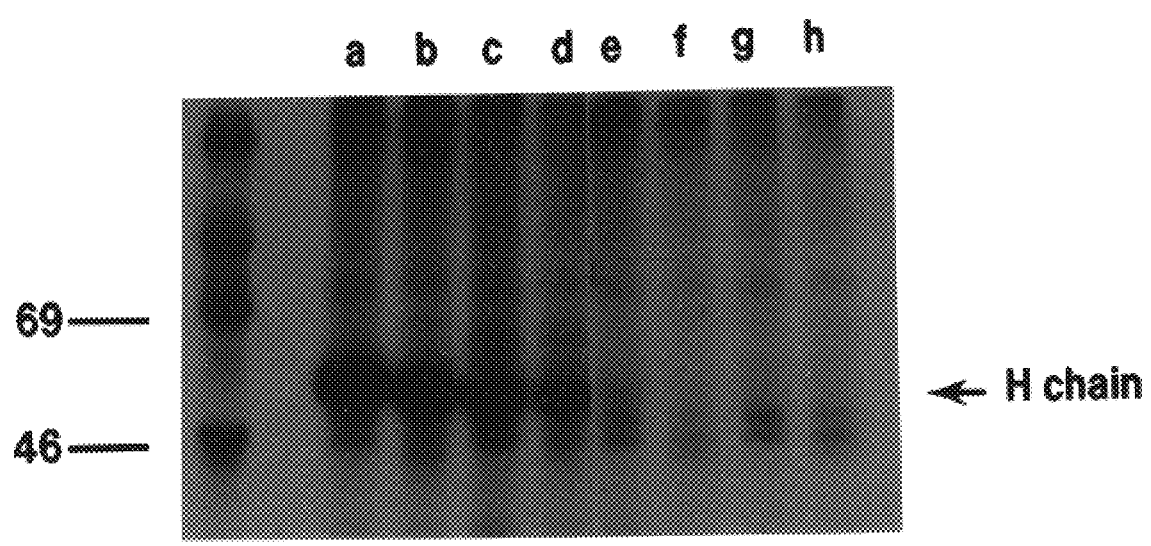
FIG. 7: Expression of the heavy chain without the signal peptide of the Y13-259 monoclonal antibody in 44-9-1-1 cells. Cells were labelled with $^{35}$S methionine and cysteine for 3½ hours. Extracts were made under nondenaturing conditions (see discussion herein below in materials and methods). The same number of trichloroacetic acid precipitable counts of each extract was incubated with rabbit anti rat serum. Track a) E89-6-19 cells, track b) E89-6-19 cells treated with tunicamycin track c) B11-9-8 cells, track d) B11-9-8 cells treated with tunicamycin, track e) NIH3T3 cells, track f) NIH3T3 cells treated with tunicamycin. The immunoprecipitates were analysed by PAGE in a 15% gel.

44-9-1-1 cells were cotransfected with pXM27, which code for the heavy chain without the signal peptide, and pHygro. Colonies were obtained after 14 days of selection and the expression of the heavy chain was tested by immunoprecipitation. A colony that expressed the highest levels was selected and named B11-9-8. The expression of the heavy chain without the signal peptide can be observed in FIG. 7. In this experiment, N-glycosylation was also tested. Tracks a and b show the heavy chain with signal peptide in the absence and presence of tunicamycin. In this case, a distinctive molecular weight shift can be observed. However, the heavy chain without the signal peptide does not show any change in molecular weight (Tracks c and d), indicating that N-glycosylation of the heavy chain is not taking place in the cytoplasm. Tracks e and f show no background proteins in the presence or absence of tunicamycin when immunoprecipitated with rabbit anti rat antibodies.

H. Transfection of B11-9-8 cells with the light chain of monoclonal antibody Y13-259 without the signal peptide B11-9-8 cells were cotransfected with pXM16, which, as already indicated, codes for the light chain of the monoclonal antibody Y13-259 without the signal peptide; its expression is under the control of the MMTV promoter, which is a promoter inducible by Dexamethasone, and pSV2 neo, a plasmid coding for the neomycin resistance gene. Colonies were obtained after 14 days of selection in the presence and absence of $10^{-7}$M Dexamethasone. Colonies that showed a change in morphology from a transformed to a nontransformed phenotype in the presence of Dexamethasone were picked and grown.

Figure 8A:
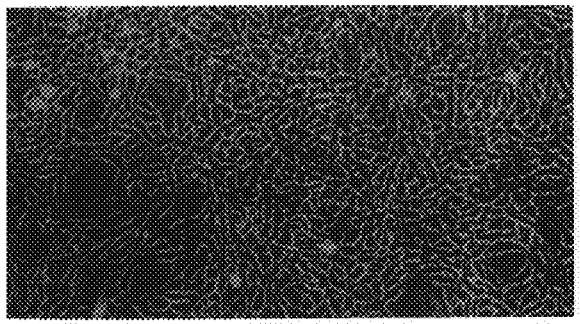
FIG. 8: Morphological changes of M13-1-1 cells in the presence and absence of dexamethasone. A and B, NIH3T3 cells in the absence and presence of dexamethasone; C and D, 44-9-1-1 cells in the absence and presence of dexamethasone; E and F, B11-9-8 cells in the absence and presence of dexamethasone; G and H, M13-1-1 cells in the absence and presence of dexamethasone. All cells were grown for a period of 5 days in the absence or presence of $10^{-7}$M dexamethasone.
Figure 8B:
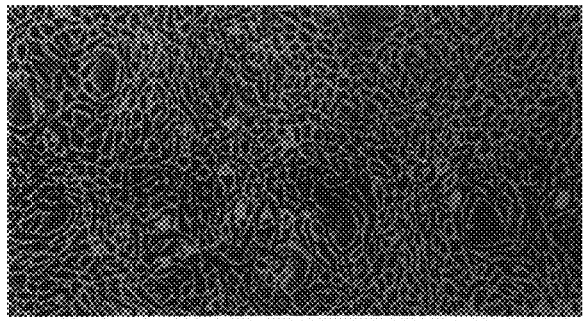
Figure 8C:
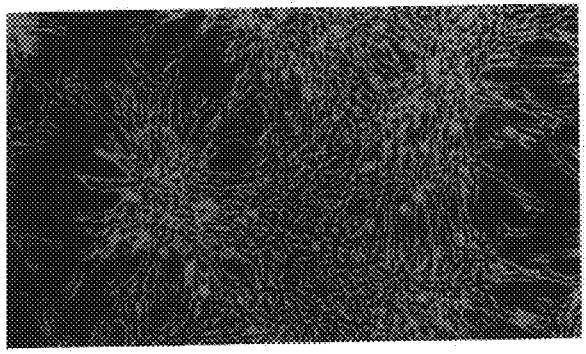
Figure 8D:
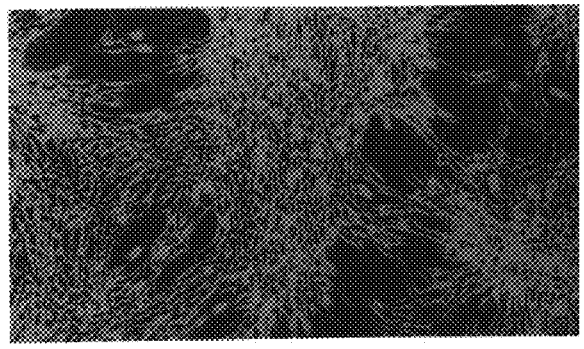
Figure 8E:
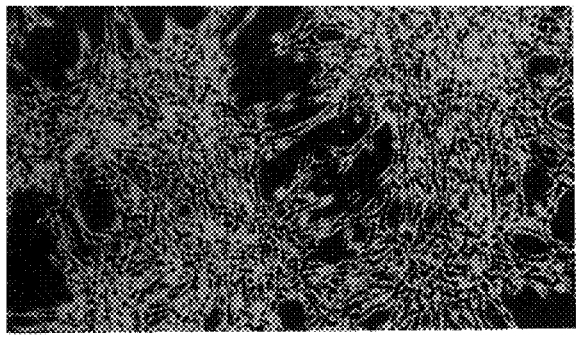
Figure 8F:
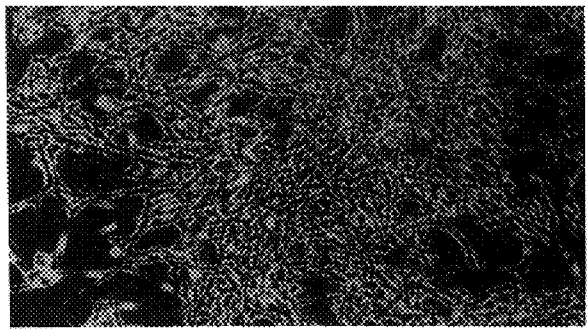
Figure 8G:
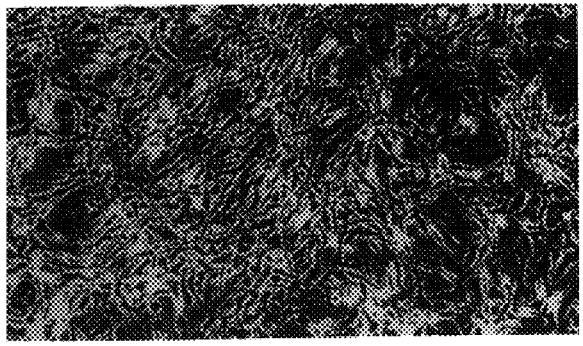
Figure 8H:
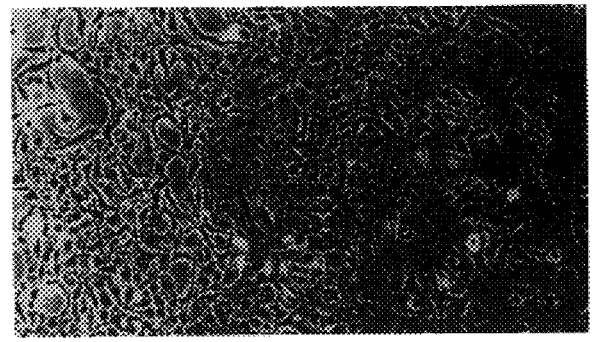

A colony was selected and denominated M13-1-1. FIG. 8 shows this result. If NIH3T3 cells are grown in the absence and presence of Dexamethasone, no morphological changes were observed. These cells kept their flat phenotype (FIGS. 8A and 8B). The same results were obtained in the case of 44-9-1-1 cells (FIGS. 8C and 8D); these cells were fusiform and refractile in both conditions. The fact that B11-9-8 cells are expressing the heavy chain without the signal peptide constitutively does not seem to induce any morphological change from a transformed to a nontransformed phenotype; similarly, no phenotypic changes take place when in the absence or presence of Dexamethasone (FIGS. 8E and 8F). However, when M13-1-1 cells were grown in the absence and presence of Dexamethasone, distinct morphological changes were observed. In the absence of Dexamethasone, these cells showed the typical fusiform phenotype and high refractibility. However, in the presence of Dexamethasone, these cells were flattened and with a tendency to hold contact inhibition which are characteristics of nontransformed cells. It is important to indicate that in the presence of Dexamethasone these cells still had the capacity to proliferate.

Figure 9A:
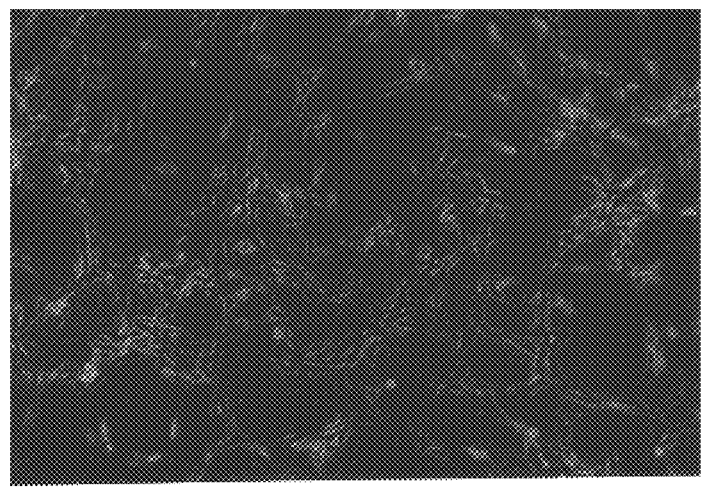
FIG. 9: Reversible morphological changes of M13-1-1 cells induced by the absence or presence of dexamethasone. A, M13-1-1 cells grown in the absence of dexamethasone; B, M13-1-1 cells grown in the presence of $10^{-7}$M dexamethasone for a period of 5 days; C, M13-1-1 cells reversed to a transformed phenotype upon withdrawal of dexamethasone.
Figure 9B:
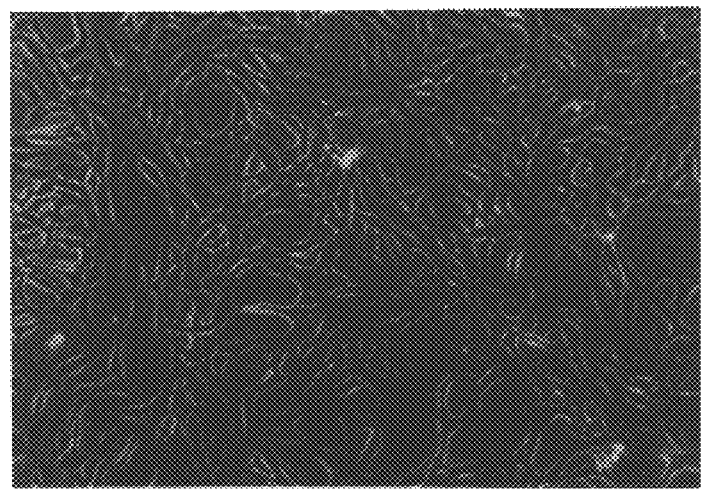
Figure 9C:
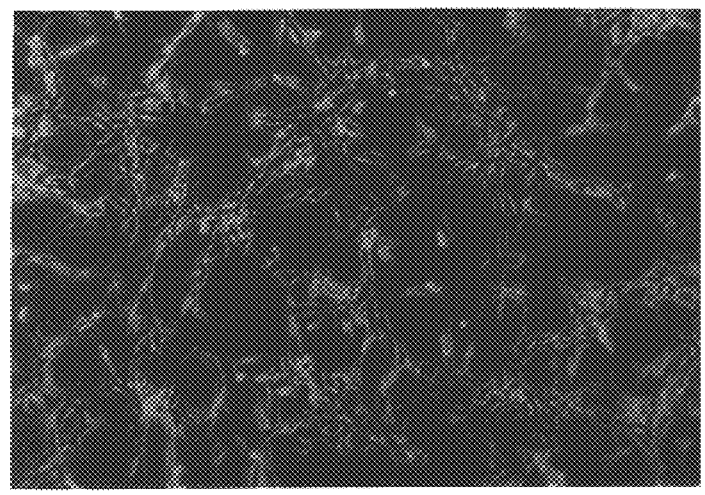

The reversion of M13-1-1 cells from a transformed to a nontransformed phenotype is not an irreversible process, as can be observed in FIG. 9C. For this experiment, cells initially grown in Dexamethasone free media (FIG. 9A) were subjected to Dexamethasone treatment for a period of 5 days (FIG. 9B). Then, when the Dexamethasone was withdrawn from the media, the cells reverted to a transformed phenotype (FIG. 9C). These changes in morphology were induced up to 4 times and the cells remained healthy.

I. Expression of the light chain of monoclonal antibody Y13-259 after induction with Dexamethasone The detection of the light chain without the secretory signal peptide of the monoclonal antibody Y13-259 was carried out by means of an ELISA, as described herein above in Materials and Methods.

Cell extracts of M13-1-1 cells grown in the presence and absence of $10^{-7}$ M Dexamethasone, as well as extracts of E89-6-19 and B11-9-8 cells, were made. The extracts were calibrated to the same protein concentration and a double serial dilution of each extract was carried out and tested for the presence of light chain protein.

Figure 10:
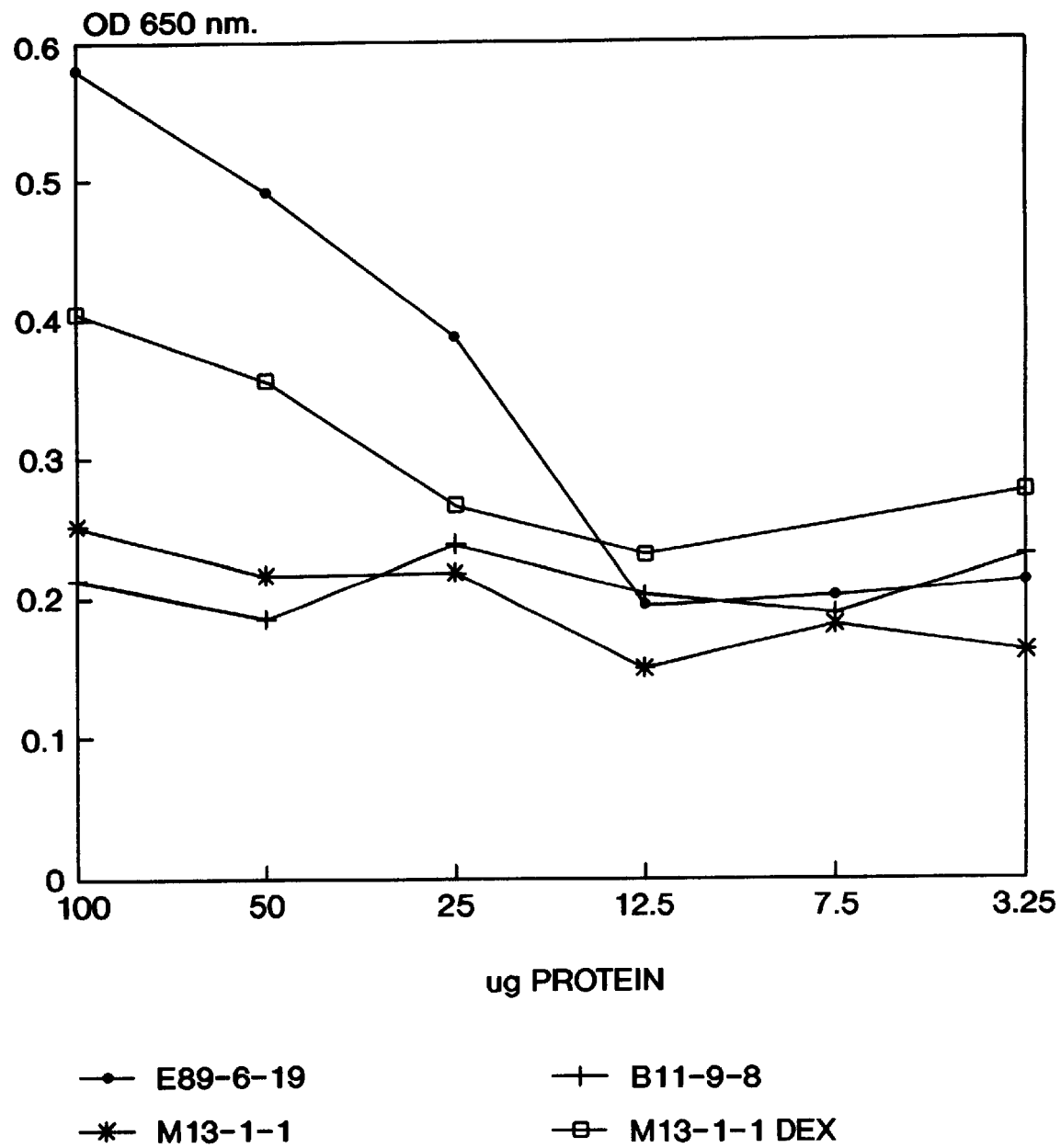
FIG. 10 shows an ELISA to detect the light (κ) chain of Y13-259 in the absence of the signal peptide.

FIG. 10 shows that the light chain expressed in M13-1-1 cells can be induced to half the concentration expressed in E89-6-19 cells. It can also be observed that barely detectable levels of light chain protein are present in noninduced M13-1-1, which resemble the kinetics seen for B11-9-8 cells, which only express the heavy chain without the signal peptide.

J. Growth Characteristics of M13-1-1 Cells

Figure 11:
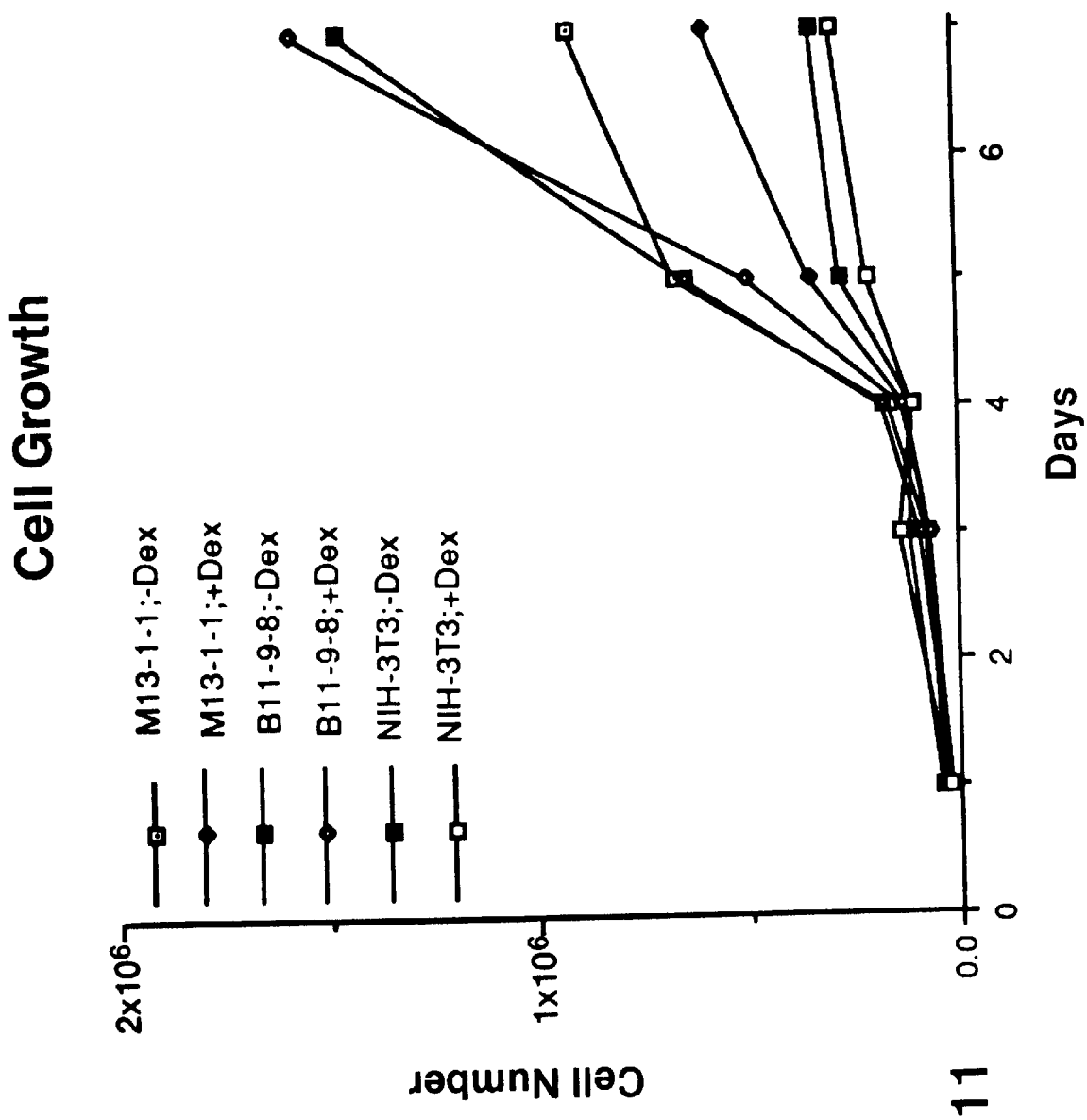
FIG. 11 shows the growth of cells expressing the Y13-259 monoclonal antibody in the absence and presence of dexamethasone.

It was also examined whether the kinetics of growth of the M13-1-1 cells expressing the heavy and light chains of the monoclonal antibody Y13-259 without the signal peptide were similar to that of NIH 3T3 cells. Cell numbers were scored for a period of 7 days for M13-1-1, B11-9-8 and NIH 3T3 cells grown in the presence and absence of Dexamethasone. In FIG. 11 the plots show that B11-9-8 cells which express the heavy chain alone grow at the same rate as the parental cell line 44-9-1-1 (data not shown) in the absence and presence of Dexamethasone. When the growth of NIH3T3 cells in the same conditions was observed, the Dexamethasone did not seem to alter their growth kinetics. However, in the case of M13-1-1 cells, a change in growth rate was observed. In the presence of Dexamethasone, the kinetics of growth was similar but not identical to that of NIH3T3 cells. In the absence of Dexamethasone, these cells grew with kinetics similar to that of B11-9-8 cells.

What is claimed is:

1. A method for inactivating the function of a protein comprising:
   a) introducing one or more recombinant DNA molecules encoding an antibody or fragment thereof which specifically binds the protein into a mammalian cell which contains the protein;
   b) expressing the recombinant DNA molecules encoding the antibody or fragment thereof intracellularly;
   c) allowing the antibody or fragment thereof to specifically bind the protein so that the function of the protein is inactivated.

2. The method according to claim 1 wherein the protein is encoded by an oncogene.

3. The method according to claim 2 wherein the protein is p21 ras protein.

4. The method according to claim 2 wherein the oncogene is selected from the group consisting of Ha-ras, K-ras, and N-ras.

5. The method according to claim 1 wherein the recombinant DNA molecules are expression vectors.

6. The method according to claim 1 wherein the antibody is a monoclonal antibody.

7. The method according to claim 1 wherein the signal peptide sequences have been deleted from the antibody.

8. The method according to claim 6 wherein the monoclonal antibody is the monoclonal antibody designated Y13-259 capable of binding p21 ras protein.

9. The method according to claim 1 or 8 wherein the recombinant DNA molecules contain all or part of the nucleotide sequences as shown in SEQ. ID NO: 1 or SEQ. ID NO: 3.

10. The method according to claim 1 wherein the cell is a neoplastic cell.

11. The method according to claim 1 wherein the cell is a transformed cell.

12. The method according to claims 10 or 11 wherein the cell is converted from a transformed phenotype to a non-transformed phenotype.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 927 base pairs
      (B) TYPE: nucleic acid
      (C) STRANDEDNESS: double
      (D) TOPOLOGY: linear (ii) MOLECULE TYPE: cDNA (ix) FEATURE:

(A) NAME/KEY: CDS
       (B) LOCATION: 1..702

(xi) SEQUENCE DESCRIPTION: SEQ ID NO:1:

```
ATG GCT ATT CCC ACT CAG CTC TTG GGG TTG TTG TTA CTG TGG ATT ACA        48
Met Ala Ile Pro Thr Gln Leu Leu Gly Leu Leu Leu Leu Trp Ile Thr
 1               5                  10                  15

GAT GCC ATA TGT GAC ATC CAG ATG ACA CAG TCT CCA CAT TCC CTG TCT        96
Asp Ala Ile Cys Asp Ile Gln Met Thr Gln Ser Pro His Ser Leu Ser
                 20                  25                  30

GCA TCT CTG GGA GAA ACT GTC TCC ATC GAA TGT CTA GCA AGT GAG GGC       144
Ala Ser Leu Gly Glu Thr Val Ser Ile Glu Cys Leu Ala Ser Glu Gly
             35                  40                  45

ATT TCC AAT TAT TTA GCG TGG TAT CAG CAG AAG CCA GGG AAA TCT CCT       192
Ile Ser Asn Tyr Leu Ala Trp Tyr Gln Gln Lys Pro Gly Lys Ser Pro
         50                  55                  60

CAG CTC CTG ATC TAT TAT GCA AGT AGC TTG CAA GAT GGG GTC CCA TCA       240
Gln Leu Leu Ile Tyr Tyr Ala Ser Ser Leu Gln Asp Gly Val Pro Ser
 65                  70                  75                  80

CGG TTC AGT GGC AGT GGA TCT GGC ACA CAG TTT TCT CTC AAG ATC AGC       288
Arg Phe Ser Gly Ser Gly Ser Gly Thr Gln Phe Ser Leu Lys Ile Ser
                 85                  90                  95

AAC ATG CAA CCT GAA GAT GAA GGG GTT TAT TAC TGT CAA CAG GCT TAC       336
Asn Met Gln Pro Glu Asp Glu Gly Val Tyr Tyr Cys Gln Gln Ala Tyr
                100                 105                 110

AAG TAT CCT TCC ACG TTT GGA GCT GGG ACC AAG CTG GAA CTG AAA CGG       384
Lys Tyr Pro Ser Thr Phe Gly Ala Gly Thr Lys Leu Glu Leu Lys Arg
            115                 120                 125

GCT GAT GCT GCA CCA ACT GTA TCC ATC TTC CCA CCA TCC ATG GAA CAG       432
Ala Asp Ala Ala Pro Thr Val Ser Ile Phe Pro Pro Ser Met Glu Gln
130                 135                 140

TTA ACA TCT GGA GGT GCC ACA GTC GTG TGC TTC GTG AAC AAC TTC TAT       480
Leu Thr Ser Gly Gly Ala Thr Val Val Cys Phe Val Asn Asn Phe Tyr
145                 150                 155                 160

CCC AGA GAC ATC AGT GTC AAG TGG AAG ATT GAT GGC AGT GAA CAA CGA       528
Pro Arg Asp Ile Ser Val Lys Trp Lys Ile Asp Gly Ser Glu Gln Arg
                165                 170                 175

GAT GGT GTC CTG GAC AGT GTT ACT GAT CAG GAC AGC AAA GAC AGC ACG       576
Asp Gly Val Leu Asp Ser Val Thr Asp Gln Asp Ser Lys Asp Ser Thr
            180                 185                 190

TAC AGC ATG AGC AGC ACC CTC TCG TTG ACC AAG GTT GAA TAT GAA AGG       624
Tyr Ser Met Ser Ser Thr Leu Ser Leu Thr Lys Val Glu Tyr Glu Arg
        195                 200                 205

CAT AAC CTC TAT ACC TGT GAG GTT GTT CAT AAG ACA TCA TCA TCA CCC       672
His Asn Leu Tyr Thr Cys Glu Val Val His Lys Thr Ser Ser Ser Pro
    210                 215                 220

GTC GTC AAG AGC TTC AAC AGG AAT GAG TGT TAGACCCAAA GGTCCTGAGG         722
Val Val Lys Ser Phe Asn Arg Asn Glu Cys
225                 230

TGCCACCTGC TCCCCAGTTC CTTCCAATCT TCCCTCCTAA GGTCTTGGAG ACTTCCCCAC     782

AAGCGACCTA CCACTGTTGC GGTGCTCCAA ACCTCCTCCC CACCTCATCC TCCTTCCTTT     842

CCTTGGCTTT GATCATGCTA ATATTTGGGG AATATTAAAT AAAGTGAATC TTTGCACTTG     902

AAAAAAAAAA AAAAAAGGA ATTCC                                            927
```

(2) INFORMATION FOR SEQ ID NO:2:

(i) SEQUENCE CHARACTERISTICS:
        (A) LENGTH: 234 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Ile Pro Thr Gln Leu Leu Gly Leu Leu Leu Leu Trp Ile Thr
 1               5                  10                  15

Asp Ala Ile Cys Asp Ile Gln Met Thr Gln Ser Pro His Ser Leu Ser
                20                  25                  30

Ala Ser Leu Gly Glu Thr Val Ser Ile Glu Cys Leu Ala Ser Glu Gly
            35                  40                  45

Ile Ser Asn Tyr Leu Ala Trp Tyr Gln Gln Lys Pro Gly Lys Ser Pro
        50                  55                  60

Gln Leu Leu Ile Tyr Tyr Ala Ser Ser Leu Gln Asp Gly Val Pro Ser
 65                  70                  75                  80

Arg Phe Ser Gly Ser Gly Ser Gly Thr Gln Phe Ser Leu Lys Ile Ser
                85                  90                  95

Asn Met Gln Pro Glu Asp Glu Gly Val Tyr Tyr Cys Gln Gln Ala Tyr
            100                 105                 110

Lys Tyr Pro Ser Thr Phe Gly Ala Gly Thr Lys Leu Glu Leu Lys Arg
        115                 120                 125

Ala Asp Ala Ala Pro Thr Val Ser Ile Phe Pro Pro Ser Met Glu Gln
130                 135                 140

Leu Thr Ser Gly Gly Ala Thr Val Val Cys Phe Val Asn Asn Phe Tyr
145                 150                 155                 160

Pro Arg Asp Ile Ser Val Lys Trp Lys Ile Asp Gly Ser Glu Gln Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Val Glu Tyr Glu Arg
        195                 200                 205

His Asn Leu Tyr Thr Cys Glu Val Val His Lys Thr Ser Ser Ser Pro
210                 215                 220

Val Val Lys Ser Phe Asn Arg Asn Glu Cys
225                 230

(2) INFORMATION FOR SEQ ID NO:3:

(i) SEQUENCE CHARACTERISTICS:
        (A) LENGTH: 765 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..765

(xi) SEQUENCE DESCRIPTION: SEQ ID NO:3:

ATG AAT TTC AGC AAC ACC TTG GTC TTC CTT TTG TTT CTT TTA AAA GGT    48
Met Asn Phe Ser Asn Thr Leu Val Phe Leu Leu Phe Leu Leu Lys Gly
 1               5                  10                  15

GTC CTG TGT GAG GTG CAG GTG CTG GAG TCT GGA GGA GGC TTA GTG CAG    96
Val Leu Cys Glu Val Gln Val Leu Glu Ser Gly Gly Gly Leu Val Gln
                20                  25                  30

CCT GGA AGG TCC CTG AAA CTC TCC TGT GTA GTC TCT GGA TTC ACT TTC   144
Pro Gly Arg Ser Leu Lys Leu Ser Cys Val Val Ser Gly Phe Thr Phe
            35                  40                  45

AGT AAC TAT GGA ATG AAC TGG ATT CGC CAG ACT CCA GGG AAG GGA CTG   192

```
Ser Asn Tyr Gly Met Asn Trp Ile Arg Gln Thr Pro Gly Lys Gly Leu
         50                  55                  60

GAG TGG GTT GCA TAC ATT AGT AGT GGT AGC AGT TAC CTC TAC TAT GCA         240
Glu Trp Val Ala Tyr Ile Ser Ser Gly Ser Ser Tyr Leu Tyr Tyr Ala
 65                  70                  75                  80

GAA ACG GTG AAG GGC CGA TTC ACC ATC TCC AGA GAC AAT GCC AAG AAC         288
Glu Thr Val Lys Gly Arg Phe Thr Ile Ser Arg Asp Asn Ala Lys Asn
                     85                  90                  95

ACC CTG TAC CTG CAA ATG ACC AGT CTG AGG TCT GAA GAC ACT GCC TTG         336
Thr Leu Tyr Leu Gln Met Thr Ser Leu Arg Ser Glu Asp Thr Ala Leu
                100                 105                 110

TAT TAC TGT GCA AGA CAT GAG GGT ACG GGT ACC GAC TTC TTT GAT TAC         384
Tyr Tyr Cys Ala Arg His Glu Gly Thr Gly Thr Asp Phe Phe Asp Tyr
            115                 120                 125

TGG GGC CAA GGA GTC ATG GTC ACA GTC TCC TCA GCT GAA ACA ACA GCC         432
Trp Gly Gln Gly Val Met Val Thr Val Ser Ser Ala Glu Thr Thr Ala
130                 135                 140

CCA TCT GTC TAT CCA CTG GCT CCT GGA ACT GCT CTC AAA AGT AAC TCC         480
Pro Ser Val Tyr Pro Leu Ala Pro Gly Thr Ala Leu Lys Ser Asn Ser
145                 150                 155                 160

ATG GTG ACC CTG GGA TGC CTG GTC AAG GGC TAT TTC CCT GAG CCA GTC         528
Met Val Thr Leu Gly Cys Leu Val Lys Gly Tyr Phe Pro Glu Pro Val
                165                 170                 175

ACC GTG ACC TGG AAC TCT GGA GCC CTG TCC AGC GGT GTG CAC ACC TTC         576
Thr Val Thr Trp Asn Ser Gly Ala Leu Ser Ser Gly Val His Thr Phe
                180                 185                 190

CCA GCT GTC CTG CAG TCT GGG CTC TAC ACT CTC ACC AGC TCA GTG ACT         624
Pro Ala Val Leu Gln Ser Gly Leu Tyr Thr Leu Thr Ser Ser Val Thr
            195                 200                 205

GTA CCC TCC AGC ACC TGG CCC AGC CAG ACC GTC ACC TGC AAC GTA GCC         672
Val Pro Ser Ser Thr Trp Pro Ser Gln Thr Val Thr Cys Asn Val Ala
210                 215                 220

CAC CCG GCC AGC AGC ACC AAG GTG GAC AAG AAA ATT GTG CCC AGA AAC         720
His Pro Ala Ser Ser Thr Lys Val Asp Lys Lys Ile Val Pro Arg Asn
225                 230                 235                 240

TGT GGA GGT GAT TGC AAG CCT TGT ATA TGT ACA GGC TCA GAA GTA             765
Cys Gly Gly Asp Cys Lys Pro Cys Ile Cys Thr Gly Ser Glu Val
                245                 250                 255

(2) INFORMATION FOR SEQ ID NO:4:

(i) SEQUENCE CHARACTERISTICS:
        (A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO:4:

Met Asn Phe Ser Asn Thr Leu Val Phe Leu Leu Phe Leu Leu Lys Gly
  1               5                  10                  15

Val Leu Cys Glu Val Gln Val Leu Glu Ser Gly Gly Gly Leu Val Gln
                 20                  25                  30

Pro Gly Arg Ser Leu Lys Leu Ser Cys Val Val Ser Gly Phe Thr Phe
             35                  40                  45

Ser Asn Tyr Gly Met Asn Trp Ile Arg Gln Thr Pro Gly Lys Gly Leu
         50                  55                  60

Glu Trp Val Ala Tyr Ile Ser Ser Gly Ser Ser Tyr Leu Tyr Tyr Ala
 65                  70                  75                  80

Glu Thr Val Lys Gly Arg Phe Thr Ile Ser Arg Asp Asn Ala Lys Asn
                     85                  90                  95
```

-continued

```
Thr Leu Tyr Leu Gln Met Thr Ser Leu Arg Ser Glu Asp Thr Ala Leu
            100             105             110

Tyr Tyr Cys Ala Arg His Glu Gly Thr Gly Thr Asp Phe Phe Asp Tyr
        115             120             125

Trp Gly Gln Gly Val Met Val Thr Val Ser Ser Ala Glu Thr Thr Ala
    130             135             140

Pro Ser Val Tyr Pro Leu Ala Pro Gly Thr Ala Leu Lys Ser Asn Ser
145             150             155             160

Met Val Thr Leu Gly Cys Leu Val Lys Gly Tyr Phe Pro Glu Pro Val
            165             170             175

Thr Val Thr Trp Asn Ser Gly Ala Leu Ser Ser Gly Val His Thr Phe
            180             185             190

Pro Ala Val Leu Gln Ser Gly Leu Tyr Thr Leu Thr Ser Ser Val Thr
        195             200             205

Val Pro Ser Ser Thr Trp Pro Ser Gln Thr Val Thr Cys Asn Val Ala
    210             215             220

His Pro Ala Ser Ser Thr Lys Val Asp Lys Lys Ile Val Pro Arg Asn
225             230             235             240

Cys Gly Gly Asp Cys Lys Pro Cys Ile Cys Thr Gly Ser Glu Val
                245             250             255
```